(12) United States Patent
Grusin (10) Patent No.: US 7,655,009 B2
(45) Date of Patent: Feb. 2, 2010

(54) HUMERAL NAIL

(75) Inventor: N. Kelley Grusin, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 855 days.

(21) Appl. No.: 10/999,572

(22) Filed: Nov. 30, 2004

(65) Prior Publication Data

US 2005/0187550 A1  Aug. 25, 2005

Related U.S. Application Data

(60) Provisional application No. 60/526,415, filed on Dec. 1, 2003.

(51) Int. Cl.
*A61B 17/56* (2006.01)

(52) U.S. Cl. .......................... 606/64; 606/66

(58) Field of Classification Search ............ 606/62–67, 606/92, 98, 289, 300–301, 316; 623/19.13–19.14, 623/20.35–20.36, 23.15, 23.23, 23.27, 23.53; 411/353, 533, 295, 85, 106, 109, 172, 222
See application file for complete search history.

(56) References Cited

U.S. PATENT DOCUMENTS

| | | | |
|---|---|---|---|
| 2,136,471 A | | 11/1938 | Schneider |
| 2,779,375 A | * | 1/1957 | O'Connor ................ 411/134 |
| 2,952,254 A | | 9/1960 | Keating |
| 2,969,994 A | * | 1/1961 | Jacobs et al. ............. 285/34 |
| 2,987,062 A | | 6/1961 | Ellison |
| 3,272,204 A | | 9/1966 | Artandi et al. |
| 3,454,072 A | * | 7/1969 | Dietlein ................. 411/109 |
| 3,463,158 A | | 8/1969 | Schmitt et al. |
| 3,531,561 A | | 9/1970 | Trebu et al. |
| 3,596,656 A | | 8/1971 | Kaute |
| 3,636,956 A | | 1/1972 | Schneider |
| 3,739,773 A | | 6/1973 | Schmitt et al. |
| 3,868,806 A | * | 3/1975 | Dey ...................... 411/353 |
| 3,876,068 A | | 4/1975 | Sonnino |
| 3,892,649 A | | 7/1975 | Phillips et al. |
| 3,896,867 A | * | 7/1975 | Gill et al. ............... 411/353 |
| 3,902,497 A | | 9/1975 | Casey |
| 3,918,100 A | | 11/1975 | Shaw et al. |
| 3,937,223 A | | 2/1976 | Roth |

(Continued)

FOREIGN PATENT DOCUMENTS

CH  669898  4/1989

(Continued)

OTHER PUBLICATIONS http://www.biometmerck.com/english/products/trauma/ankle/htm, on page, Jan. 6, 2005.

(Continued)

*Primary Examiner*—Thomas C Barrett
*Assistant Examiner*—James L. Swiger
(74) *Attorney, Agent, or Firm*—Kilpatrick Stockton LLP (57) ABSTRACT

An intramedullary nail for treating fractures of a bone includes a body having a head, an intermediate portion and a distal tip. At least one transverse opening for receiving a screw is provided in the body. The opening comprises an insert adapted to receive the screw.

16 Claims, 5 Drawing Sheets

U.S. PATENT DOCUMENTS

| | | |
|---|---|---|
| 3,960,151 A | 6/1976 | Kuhn |
| 4,067,371 A * | 1/1978 | Stencel .................. 411/107 |
| 4,135,507 A | 1/1979 | Hararis |
| 4,146,936 A | 4/1979 | Aoyagi et al. |
| 4,186,448 A | 2/1980 | Brekke |
| 4,191,185 A | 3/1980 | Lemieux |
| 4,192,021 A | 3/1980 | Deibig et al. |
| 4,219,015 A | 8/1980 | Steinemann |
| 4,279,249 A | 7/1981 | Vert et al. |
| 4,280,233 A | 7/1981 | Raab |
| 4,292,694 A | 10/1981 | Koeneman |
| 4,338,926 A | 7/1982 | Kummer et al. |
| 4,429,690 A | 2/1984 | Angelino-Pievani |
| 4,457,301 A | 7/1984 | Walker |
| 4,475,545 A | 10/1984 | Ender |
| 4,503,847 A | 3/1985 | Mouradian |
| 4,522,202 A | 6/1985 | Otte et al. |
| 4,523,591 A | 6/1985 | Kaplan et al. |
| 4,550,449 A | 11/1985 | Tunc |
| 4,612,923 A | 9/1986 | Kronenthal |
| 4,622,959 A | 11/1986 | Marcus |
| 4,655,203 A | 4/1987 | Tormala et al. |
| 4,733,654 A | 3/1988 | Marino |
| 4,751,183 A | 6/1988 | Sonneborn et al. |
| 4,756,307 A | 7/1988 | Crowninshield |
| 4,776,330 A | 10/1988 | Chapman et al. |
| 4,781,183 A | 11/1988 | Casey et al. |
| 4,790,302 A | 12/1988 | Colwill et al. |
| 4,793,757 A * | 12/1988 | Peterson .................. 411/533 |
| 4,851,008 A | 7/1989 | Johnson |
| 4,863,475 A | 9/1989 | Andersen et al. |
| 4,875,474 A | 10/1989 | Border |
| 4,875,475 A | 10/1989 | Comte et al. |
| 4,895,572 A | 1/1990 | Chernoff |
| 4,896,661 A | 1/1990 | Bogert et al. |
| 4,898,186 A | 2/1990 | Ikada et al. |
| 4,906,153 A * | 3/1990 | Duran .................. 411/353 |
| 4,911,153 A | 3/1990 | Border |
| 4,919,666 A | 4/1990 | Buchhorn et al. |
| 4,943,292 A | 7/1990 | Foux |
| 4,964,403 A * | 10/1990 | Karas et al. .................. 606/60 |
| 4,968,317 A | 11/1990 | Tormala et al. |
| 4,973,333 A | 11/1990 | Treharne |
| 4,976,258 A | 12/1990 | Richter et al. |
| 4,989,186 A | 1/1991 | Ricker |
| 5,009,664 A | 4/1991 | Sievers |
| 5,034,013 A | 7/1991 | Kyle et al. |
| 5,035,697 A | 7/1991 | Frigg |
| 5,041,114 A | 8/1991 | Chapman et al. |
| 5,057,110 A | 10/1991 | Kranz et al. |
| 5,057,111 A | 10/1991 | Park |
| 5,066,296 A | 11/1991 | Chapman et al. |
| 5,084,050 A | 1/1992 | Draenert |
| 5,084,051 A | 1/1992 | Tormala et al. |
| 5,108,399 A | 4/1992 | Eitenmuller et al. |
| 5,112,333 A | 5/1992 | Fixel |
| 5,123,911 A | 6/1992 | Granger et al. |
| 5,127,913 A | 7/1992 | Thomas, Jr. |
| 5,190,546 A | 3/1993 | Jervis |
| 5,201,735 A | 4/1993 | Chapman et al. |
| 5,236,431 A | 8/1993 | Gogolewski et al. |
| 5,248,313 A | 9/1993 | Greene et al. |
| 5,250,049 A | 10/1993 | Michael |
| 5,263,431 A | 11/1993 | Wood |
| 5,269,784 A | 12/1993 | Mast |
| 5,275,601 A | 1/1994 | Gogolewski et al. |
| 5,292,695 A | 3/1994 | Galloway |
| 5,413,577 A | 5/1995 | Pollock |
| 5,441,500 A | 8/1995 | Seidel et al. |
| 5,472,444 A | 12/1995 | Huebner et al. |
| 5,484,438 A | 1/1996 | Pennig |
| 5,501,695 A | 3/1996 | Anspach, Jr. et al. |
| 5,514,137 A | 5/1996 | Coutts |
| 5,520,690 A | 5/1996 | Errico et al. |
| 5,534,027 A | 7/1996 | Hodorek |
| 5,549,610 A | 8/1996 | Russell et al. |
| 5,569,250 A | 10/1996 | Sarver et al. |
| 5,584,836 A | 12/1996 | Ballintyn et al. |
| 5,603,715 A | 2/1997 | Kessler |
| 5,618,286 A | 4/1997 | Brinker |
| 5,658,287 A | 8/1997 | Hofmann et al. |
| 5,662,472 A | 9/1997 | Grutzner |
| 5,720,766 A | 2/1998 | Zang et al. |
| 5,725,541 A | 3/1998 | Anspach, III et al. |
| 5,730,744 A | 3/1998 | Justin et al. |
| 5,741,258 A | 4/1998 | Klaue et al. |
| 5,741,266 A | 4/1998 | Moran et al. |
| 5,741,282 A | 4/1998 | Anspach, III et al. |
| 5,743,914 A | 4/1998 | Skiba |
| 5,776,194 A | 7/1998 | Mikol et al. |
| 5,792,400 A | 8/1998 | Talja et al. |
| 5,810,821 A | 9/1998 | Vandewalle |
| 5,810,823 A | 9/1998 | Klaue et al. |
| 5,836,949 A | 11/1998 | Campbell, Jr. et al. |
| 5,855,579 A | 1/1999 | James et al. |
| 5,868,746 A | 2/1999 | Sarver et al. |
| 5,871,484 A | 2/1999 | Spievack et al. |
| 5,876,402 A | 3/1999 | Errico et al. |
| 5,879,389 A | 3/1999 | Koshino |
| 5,895,390 A | 4/1999 | Moran et al. |
| 5,902,303 A * | 5/1999 | Eckhof et al. .................. 606/60 |
| 5,904,683 A | 5/1999 | Pohndorf et al. |
| 5,925,077 A * | 7/1999 | Williamson et al. ...... 623/22.34 |
| 5,927,978 A | 7/1999 | Muller |
| 5,928,267 A | 7/1999 | Bonutti et al. |
| 5,931,838 A | 8/1999 | Vito |
| 5,935,127 A | 8/1999 | Border |
| 5,976,141 A * | 11/1999 | Haag et al. .................. 606/292 |
| 6,004,323 A | 12/1999 | Park et al. |
| 6,015,937 A | 1/2000 | Branemark |
| 6,019,761 A | 2/2000 | Gustilo |
| 6,030,389 A | 2/2000 | Wagner et al. |
| 6,053,918 A | 4/2000 | Spievack |
| 6,106,528 A | 8/2000 | Durham et al. |
| 6,120,504 A | 9/2000 | Brumback et al. |
| 6,123,708 A | 9/2000 | Kilpela et al. |
| 6,168,595 B1 | 1/2001 | Durham et al. |
| 6,197,029 B1 | 3/2001 | Fujimori et al. |
| 6,228,086 B1 | 5/2001 | Wahl et al. |
| 6,235,033 B1 | 5/2001 | Brace et al. |
| 6,248,108 B1 | 6/2001 | Tormala et al. |
| 6,261,291 B1 | 7/2001 | Talaber et al. |
| 6,270,304 B1 | 8/2001 | Freedland |
| 6,296,645 B1 | 10/2001 | Hover et al. |
| 6,309,392 B1 | 10/2001 | Alexander et al. |
| 6,319,253 B1 | 11/2001 | Ackeret et al. |
| 6,368,319 B1 | 4/2002 | Schaefer |
| 6,383,187 B2 | 5/2002 | Tormala et al. |
| 6,443,954 B1 | 9/2002 | Bramlet et al. |
| 6,488,684 B2 | 12/2002 | Bramlet et al. |
| 6,524,314 B1 * | 2/2003 | Dean et al. .................. 606/64 |
| 6,572,620 B1 | 6/2003 | Schon et al. |
| 6,572,655 B1 | 6/2003 | Johnson |
| 6,575,975 B2 | 6/2003 | Brace et al. |
| 6,579,293 B1 | 6/2003 | Chandran |
| 6,602,255 B1 | 8/2003 | Campbell et al. |
| 6,605,090 B1 | 8/2003 | Trieu et al. |
| 6,626,906 B1 | 9/2003 | Young |
| 6,673,116 B2 | 1/2004 | Reiley |
| 6,709,436 B1 | 3/2004 | Hover et al. |
| 6,730,093 B2 | 5/2004 | Saint Martin |
| 6,755,834 B2 | 6/2004 | Amis |
| 6,783,529 B2 | 8/2004 | Hover et al. |
| 6,786,908 B2 | 9/2004 | Hover et al. |

| | | | |
|---|---|---|---|
| 6,979,334 | B2 | 12/2005 | Dalton |
| 7,247,157 | B2 * | 7/2007 | Prager et al. .................. 606/64 |
| 2001/0021851 | A1 | 9/2001 | Eberlein et al. |
| 2001/0031966 | A1 | 10/2001 | Tormala et al. |
| 2001/0037112 | A1 | 11/2001 | Brace et al. |
| 2002/0029041 | A1 | 3/2002 | Hover et al. |
| 2002/0062128 | A1 | 5/2002 | Amis |
| 2002/0072748 | A1 | 6/2002 | Robioneck |
| 2002/0133156 | A1 * | 9/2002 | Cole ........................... 606/62 |
| 2002/0133158 | A1 | 9/2002 | Saint Martin |
| 2002/0151898 | A1 | 10/2002 | Sohngen et al. |
| 2003/0009219 | A1 | 1/2003 | Seyr et al. |
| 2003/0018336 | A1 | 1/2003 | Vanderwalle |
| 2003/0069581 | A1 | 4/2003 | Stinson et al. |
| 2003/0078583 | A1 | 4/2003 | Biedermann et al. |
| 2003/0187440 | A1 | 10/2003 | Richelsoph et al. |
| 2003/0195515 | A1 | 10/2003 | Sohngen |
| 2003/0199876 | A1 | 10/2003 | Brace et al. |
| 2004/0030342 | A1 | 2/2004 | Trieu et al. |
| 2004/0092942 | A1 | 5/2004 | Reiley |
| 2004/0097935 | A1 | 5/2004 | Richelsoph et al. |
| 2004/0127899 | A1 | 7/2004 | Konieczynski et al. |
| 2004/0127900 | A1 | 7/2004 | Konieczynski et al. |
| 2004/0127904 | A1 | 7/2004 | Konieczynski et al. |
| 2004/0158252 | A1 | 8/2004 | Prager et al. |
| 2004/0260290 | A1 | 12/2004 | Zander et al. |
| 2006/0100623 | A1 | 5/2006 | Pennig |
| 2007/0123878 | A1 | 5/2007 | Shaver et al. |
| 2008/0287949 | A1 | 11/2008 | Keith et al. |

FOREIGN PATENT DOCUMENTS

| | | |
|---|---|---|
| DE | 1949923 | 4/1971 |
| DE | 196 29 011 A1 | 1/1998 |
| DE | 19945611 | 9/2001 |
| DE | 203 00 987 U1 | 4/2003 |
| DE | 203 09 399 U1 | 8/2003 |
| EP | 0 299 004 B1 | 1/1989 |
| EP | 0 355 411 A1 | 2/1990 |
| EP | 0 491 983 A1 | 7/1992 |
| EP | 0 583 442 B1 | 2/1994 |
| EP | 0633750 | 8/1994 |
| EP | 0 710 091 B2 | 5/1996 |
| EP | 0876128 | 12/1996 |
| EP | 0776636 | 6/1997 |
| EP | 0874593 | 7/1997 |
| EP | 1196103 | 1/2001 |
| EP | 1 169 971 A2 | 1/2002 |
| EP | 1169971 | 1/2002 |
| EP | 1 415 604 A1 | 5/2004 |
| FR | 2 710 835 | 4/1995 |
| GB | 2392096 | 2/2004 |
| SU | 1692566 A1 | 11/1991 |
| WO | WO 96/35387 | 11/1996 |
| WO | WO 98/41161 | 9/1998 |
| WO | WO 98/46169 | 10/1998 |
| WO | 9905968 | 2/1999 |
| WO | WO 99/05968 | 2/1999 |
| WO | WO 00/61018 | 10/2000 |
| WO | 0178615 | 10/2001 |
| WO | WO 03/017822 | 3/2003 |

OTHER PUBLICATIONS

DePuy website paper entitled The VersaNail System: A Versatile Ankle Fusion Option, pp. 1-3 (copyright 2002-2004).
EBI Products website paper entitled "Excellence By Innovation" one page (undated).
Dr. Rodriguez's www.chicagofootandanklesurgery.com (Ankle Fusion) web page, pp. 1-3 (Mar. 11, 2005 http://www.cfaas.com/anklefusion.htm.
Encore: True/Fix® Proximal Humeral Nail web page, pp. 1-2, Jan. 19, 2005 http://www.encoremed.com/orthopedics/products/trauma/proximal_humeral_nail.html.
Orthofix Retrograde Nailing System , 'The long and the short of it,' Orthofix Always Inovating Brochure, 10 pages, 2002.
Orthofix Operative Technique Brochure entitled 'The Ankle Arthrodesis Nail,' by Profs. Dr. D. Pennig, 16 pages, 2002.
Smith & Nephew Brochure entitled "Intramedullary Supracondylar Nail Surgical Technique," by David Seligson, M.D., et al., pp. 1-29 (Mar. 1998).
"Alta Modular Trauma System . . . The leading edge in fracture management technology . . . the alta® tibial/humeral rod module for reamed and non-reamed procedures," 10 pages Jan. 1992.
Biomet, Inc. Brochure 'UNIFLEX® Surgical Technique,' pp. 1-12, 1995.
Biomet, Inc. Medical Products Brochure, 'UNIFLEX® Nailing System, pp. 1-14 (1995).
Biomet, Inc. Medical Products Brochure, Trauma Systems UNIFLEX™ Tibial Nail System, 4 pages (1995).
Biomet, Inc. Brochure 'UNIFLEX® Surgical Technique,' pp. 1-16, 1995.
Biomet Inc. Vector Intertrochanteric Nail, Version Two, 19 pages, 1995.
Biomet Inc., Biomet Retrograde Femoral Nail, 6 pages, 1995.
Biomet Inc., Biomet Retrograde Femoral Nail Surgical Technique, 12 pages, 1995.
Biomet Inc., AIM™ Titanium Femoral Nail, 11 pages, 1995.
Biomet, Inc., Vector Intertrochanteric Nail, Version One, 18 pages, 1995.
Brochure of Intramedullary Nail. One Nail . . . Diaphyseal Fractures.
URTN System Introduction, "The Titanium Unreamed Tibial Nail System: the next generation in Unreamed Tibial Nails from SYNTHES and the AO/ASIF," one page.
Parts List, undated.
Biomet Medical Products Inc. 'Interlocking Nail,' 14 pages, 1995.
Craig B. Ordway, Surgical Technique, AIM Titanium Femoral Nail System, New York, pp. 1-11.
Ferguson, et al., 'Finite element stress analysis of a hybrid fracture fixation plate,' Med. Eng. Phys., 10(5):241-250 (1996).
Foux, et al., 'Improved Fracture Healing with Less Rigid Plates A Biomedical Study In Dogs,' Clinical Orthopaedics and Related Research, 339:232-245 (1997).
Hofmann, 'Editorial Biodegradable Implants in Orthopaedic Surgery,' Clinical Materials, 10:1 Table of Contents (1992).
Kato, et al., The Weakest Link in the Bone Plate Fracture System: Changes with Time, Clinical and Laboratory Performance of Bone Plates, ASTM STP 1217, ed. By Harvey and Games, pp. 85-94 (1994).
McKellop, et al., Development and Clinical Performance of a Reversible Titanium Alloy Femoral Intramedullary Nail, Scientif Exhibit #3512, American Academy of Orthopaedic Surgeons, 58th Annual Meeting, Mar. 7-11, 1991.
Nazre, et al., 'Theoretical Strength Comparison of Bioabsorbable (PLLA) Plates and Conventional Stainless Steel and Titanium Plates Used in Internal Fracture Fixation,' Clinical and Laboratory Performance of Bone Plates, ASTM STP 1217, J.P. Harvey, Jr., and R. F. Games, Eds., American Society for Testing and Materials, Philadelphia, 1994, pp. 53-64.
Raiha, 'Biodegradable Implants as Intramedullary Nails. A Survey of Recent Studies and an Introduction to Their Use,' Clinical Materials, 10:35-39 (1992).
Rommens, et al., "Retrograde locked nailing of humeral shaft fractures: A review of 39 patients," *J. Bone Joint Surg. Br.*, 77(4):667 (1995) http://www/ncbi.nlm.nih.gov/entrez/query.fcgi?cmd=Retrieve&db=PubMed&dopt=Abstra . . . .
Simon, et al., Bioresorbable Fracture Fixation in Orthopedics : a Comprehensive Review. Part II. Clinical Studies, The American Journal of Orthopedics, pp. 754-762 (Nov. 1997).
Yeadon, et al., 'Influence of Axially Flexible Plates on Bone Healing: A Biomedical Study in Canine Femora,' CMBES 20 CCGB Vancouver 1994, pp. 34-35.
Brochure entitled Stryker T2 TM Proximal Humeral Nailing System Operative Technique Stryker Trauma®, 20 pages (2003).
Abstract DE10015734 published Sep. 13, 2001, Med Medical Engineering Dev. LT.

* cited by examiner

HUMERAL NAIL

RELATED APPLICATION

The present application claims the benefit of provisional patent application Ser. No. 60/526,415 filed on Dec. 1, 2003 entitled "Humeral Nail," the contents of which are incorporated herein by reference.

FIELD OF THE INVENTION

The present invention relates generally to systems for attachment of bones or bone segments to each other. More specifically, the present invention relates to intramedullary systems for coupling bone portions across a fracture and, particularly, to intramedullary nails and screw assemblies for treatment of humeral fractures. More particularly, devices according to aspects and embodiments of the invention reduce undesired movement of components of an intramedullary system used in treatment of a bone fracture, thereby decreasing the risk of the fracture becoming unreduced, decreasing the risk of damage of the bone and soft tissues, and, generally, reducing healing time.

BACKGROUND

A variety of devices are conventionally used to treat bone fractures. Intramedullary nail systems (also known as intramedullary rod systems) are employed in orthopedic surgery for repairing fractures of long bones, such as the femur and humerus. Use of intramedullary nail systems reduces healing time, permits less immobilization of the affected limb, and simplifies treatment of complex fractures.

An example of a conventional intramedullary nail used for humeral repair generally takes the form of an elongated cannulated body. At various locations along its length, the nail is provided with one or more transverse openings for receiving screws. Typically, at least one transverse opening is located near an end of the nail. The openings are commonly adapted to receive the screws at various angles in order to repair a wide range of fractures in a variety of patients using the same nail design. The nail is normally provided with a securing arrangement on at least one end. The securing arrangement is for securing a tool or device for inserting and extracting the nail, as well as maintaining the nail's desired position during insertion. In order to facilitate correct insertion of the nail into a medullary canal, various guiding devices and arrangements are used. Examples of such arrangement are guiding wires, sleeves, or pins.

To repair a bone fracture using an intramedullary nail system, a medullary canal of the bone is reamed using an appropriate tool or device. An intramedullary nail is inserted into the medullary canal and advanced axially through the canal so that the nail traverses the fracture site. Then, one or more screws or pins are applied to the nail through the transverse openings in the nail. The screws extend through the bone on one or both sides of the fracture site so that the nail is attached to portions of the bone on each side of the fracture, thereby securing the bone segments and allowing healing along the fracture site.

One of the problems commonly associated with the intramedullary nail systems is insufficient retention of the screws or pins in the nail, which causes undesirable movement in the system. Detrimental to healing consequences of such undesirable movement include but are not limited to, the fracture becoming unreduced, collapse of parts of the bone onto each other, or damage to bones or soft tissues by bone parts or parts of the system.

Intramedullary nail systems are commonly designed to allow insertion of the screws or pins in the nail at various angles. In one aspect, this feature ensures an ability to use the same nail to repair various fractures in bones in a range of sizes and shapes. This eliminates the necessity to have available different types of intramedullary nail systems, each allowing insertion of screws at specific angles. In another aspect, the ability to vary the angle of insertion of a screw into an opening in the nail allows to compensate for misalignments that occur during surgery.

There are, however, problems associated with the openings capable of receiving screws at a range of angles. Particularly, this feature leads to wobbling of the end of the screw inserted in the nail. For stabilization, the screw relies on purchase of its other end to the bone tissue. The undesirable movement occurs if the purchase to the bone tissue is inadequate, or is lost after the reduction of the fracture. Moreover, wobbling of the end of the screw inserted in the nail increases the tension applied by the other end of the nail to the bone tissue and may facilitate the destruction of the bone tissue.

Long bones such as femur and humerus can be fractured in the lower portion, the mid portion or the upper portion, where the bone connects to the joint. The third scenario is typically referred to as a proximal fracture. Proximal fractures of long bones, such as femur or humerus, frequently occur in women with osteoporosis, a condition of brittle, fragile bones. Osteoporosis is highly prevalent in women, especially in those post menopause, thus making repair of the proximal fractures of femur and humerus an important public health issue.

The repair of proximal humeral fractures using intramedullary nails is especially difficult. In proximal humerus, the bone is mostly cancellous and of relatively low density. Due to poor bone quality, adequate stabilization of the humeral head or tuberosities during bone fracture repair is challenging and is not provided by currently available intramedullary nail systems and techniques.

Traditional humeral nails use one or two proximal screws for fixation. To reduce a fracture, these constructs rely on purchase of screw threads to the bone in order to hold the fragments of the bone together. When the thread purchase in the bone is lost, the fracture becomes unreduced. Additionally, the loose screws cause damage to the surrounding bone and the soft tissues.

Other currently available nails for repair of proximal humeral fractures use multiple non-coplanar screws for proximal fixation. These designs are less dependent upon thread purchase due to the use of diverging or converging fixation pattern. By having two non-coplanar screws attached to a single bone fragment, the pullout forces are directed away from axes of each the screws. These constructs rely on fixation of the screws to bone tissue, which can lead to the deterioration of the bone tissue.

Both types of constructs described above require sufficient amount and quality of bone tissue for fixation of the fracture. When the bone tissue is lost due to disease or a pathological condition or for other reasons, the constructs become unstable. Persons with thin or fragile bones, such as osteoporosis patients, avascular necrosis patients and patients with metastatic bones, are particularly prone to fractures. Therefore, currently available intramedullary nail systems do not satisfy the requirements of the patients who are in particular need of such constructs.

In view of the foregoing, there is a need for intramedullary nail systems which provide increased stabilization of screws in an intramedullary nail, while simultaneously allowing insertion of the screws into the nail at a range of angles. There is also a need for intramedullary nail systems which reduce undesirable movement in a bone fracture stabilized with the system, and reduce undesirable movement of the components of the system with respect to each other. Ability of an intramedullary nail system to reduce the fractures of bones of poor quality, such as those occurring during osteoporosis, cancer or other pathological conditions, is also desirable. In general, there is a need for intramedullary nail systems which are versatile, allow for faster healing with fewer complications, require less immobilization, are easy to use and manufacture, and are less costly to produce and operate.

SUMMARY

The current invention provides methods and apparatuses for stabilization of screw assemblies used in attachment of bones or bone segments or fragments to each other. Particularly, the current invention provides methods and apparatuses useful in repair of bone fractures, especially those of long bones or large tubular bones. Methods and apparatuses of the present invention are especially suitable for repair of bone fractures where the increased stability of the screw assemblies is desirable. Included within the scope of the present invention is the use of the methods and apparatuses of the present invention in any method of repair or attachment of bones and other tissues where increased stability of the screw construct is advantageous.

The current invention solves the problems of screw stabilization in screw assemblies used in attachment of bones or bone fragments to each other by incorporating into the assemblies inserts or bushings for stabilization of screws. In a preferred embodiment, the inserts or bushings provide increased stabilization of a screw construct.

In one aspect, structures according to an embodiment of the present invention provide an intramedullary nail system, comprising at least one screw and an intramedullary nail, which comprises at least one opening with an insert or bushing, wherein the insert or bushing increases retention of the screw in the opening of the intramedullary nail as compared to conventional system, while permitting insertion of the screw in the opening at a range of angles. In another aspect, the current invention provides an improved construct of an intramedullary nail, comprising at least one opening with an insert, which allows for increased retention of a screw in the opening of the intramedullary nail, at the same time permitting insertion of the screw in the opening at a range of angles. In one more aspect, the current invention provides an insert for use in screw constructs used in stabilization of bones or bone fragments. The insert of the present invention allows insertion at a range of angles of screws used in stabilization of bones or bone fragments. Additionally, the current invention provides a method of reducing fractures of bones using the improved intramedullary nail system of the present invention.

An advantage of intramedullary nail systems of certain aspects and embodiments of the present invention is decreased undesirable movement of the components of the system with respect to each other. Another advantage of certain aspects and embodiments of the present invention is the decreased undesirable movement of tissues stabilized with the systems of the present invention with respect to each other and the system or its components. Intramedullary nail systems of certain aspects and embodiments of the present invention are advantageously used for reduction of fractures of bones of poor quality, such as those occurring during diseases and pathological conditions. The intramedullary nail systems of certain aspects and embodiments of the present invention are versatile and easy to operate.

Various devices according to embodiments of the invention can be advantageously used in the treatment of a variety of bone fractures, including, but not limited to, open or compound fractures, closed fractures, complete fractures, incomplete fractures, transverse fractures, spiral or oblique fractures, comminuted fractures, compression fractures, impacted fractures, avulsion fractures, pathological fractures, torus, or a greenstick, or ripple fractures, stress fractures, fractures of the diaphyseal, of proximal and distal or malleolar segment of long bones, including, but not limited to, fractures of femur, humerus, tibia, fibula, radius or ulna, multifragmentary fractures, including but not limited to wedge fractures or complex fractures, extra-articular fractures, articular fractures, fractures of proximal humerus, such as extra-articular unifocal, extra-articular bifocal, and articular, fractures of proximal femur, such as fractures of trochanteric area, neck, head, or malleolar segment, including but not limited to infrasydesmotic, transsyndesmotic and suprasyndesmotic fractures, epiphyseal, metaphyseal, and diaphyseal fractures, or any combination or variation thereof.

The systems of certain aspects and embodiments of the present invention are advantageously used in treatment of fractures associated with the diseases and pathological conditions that can lead to or be associated with low bone density and general poor quality of bone tissue. The diseases and conditions include, but are not limited to, bone neoplasms, osteitis deformans, osteochondritis, osteonecrosis, bone demineralization, tuberculosis, osteoporosis, or any combination or variation thereof.

The intramedullary nail systems of certain aspects and embodiments of the present invention are versatile, allow for faster healing with less complications and require less immobilization compared to conventional systems. Such systems are easy to manufacture, and are less costly than conventional systems to produce and operate.

In accordance with certain aspects and embodiments of the present invention, a system for treating fractures of a bone comprises an intramedullary nail and at least one screw. The intramedullary nail takes a form of a cannulated tube, which is rigid axially and torsionally. The intramedullary nail is approximately 8 mm to approximately 11 mm in diameter and approximately 16 cm to approximately 28 cm in length. The intramedullary nail has a cross-section with a lateral side and a medial side. It comprises one or more transverse openings for receiving a screw. In a preferred embodiment of the present invention, the intramedullary nail comprises 1 to 4 openings. The openings are located at various locations along the length of the nail and extend at various angles relative to the anterior/posterior, superior/inferior, and medial/lateral axes of the nail, so that the same nail can be used for repair of a range of fractions at various locations of the bone. The screw comprises two ends and is adapted to engage the bone at one end and the nail at another end, thereby attaching the bone to the nail. The opening is adapted to receive the screw and is at least partially threaded in order to engage the screw.

A distinguishing feature of certain aspects and embodiments of the present invention is that an insert for receiving a screw is incorporated in the non-threaded part of the opening. The insert provides additional stabilization to the screw engaged by the threads of the opening. The insert is made of a suitable polymer material, including but not limited to high density polyethylene, a bioresorbable material, such as poly-l lactic acid, silicone, polyetheretherketone (PEEK) with or without composite fibers, nitinol, bone cement, or a biologic, such as calcium sulfate. The use of other materials, including but not limited to, composite materials and non-polymer materials, is also envisioned. In a preferred embodiment of the present invention, the material of which the insert is made is preferably sufficiently strong to support the load of the screw, but sufficiently soft to accept the threads of the screw, with a hardness of approximately 60 to approximately 70 on Shore D scale.

In a preferred embodiment of the present invention, both the insert and the threads are employed to engage the screw in the nail. In a preferred configuration, the lateral side of the opening is threaded. The screw inserts through the lateral side of the opening and engages the threads. The relative sizes of threads of the opening and the screw are adapted to allow insertion of the screw at a range of angles. A major diameter of the opening is approximately 0.010" larger than a major diameter of the screw. Crest width along the major diameter of the opening is approximately five times wider than crest width along the major diameter of the screw. The above feature facilitates loose fit of the screw in the opening and allows compensation for mismatches in alignment. As the screw exits the threaded part of the opening, it enters the insert. In a preferred embodiment of the present invention, the insert is hollow and pre-threaded, with threadform of the insert closely matching threadform of the screw. The above feature stabilizes the screw in the insert.

Variations on the above configuration are envisioned and fall within the scope of the present invention. Examples of nonlimiting alternative configurations are as follows. In one configuration, the insert is placed in the opening of the intramedullary nail so that the screw is received by and passes through the insert before being received and engaged by the threads. In another configuration, the insert is the sole means of engaging and stabilizing the screw in the opening. In yet another configuration, the insert is combined with any additional means of engaging and holding the screw in the nail. An example of additional means of engaging and holding the screw in the nail is removing the sleeve and injecting a biologic or bone cement through a proximal cannulation as each screw is inserted, starting with the most distal of the proximal screws. The injected material fills in the cavity where the insert is located.

The insert is adapted to fit tightly inside the opening. Preferably, means for stabilizing the insert in the opening are provided. In a preferred embodiment, the insert is stabilized in the opening by a circumferential rib or a locking ring which fits into a corresponding groove in the opening. Other configurations for stabilization of the insert in the opening are envisioned and fall within the scope of the present invention. The examples of such configurations include, but are not limited to, an interference fit, such as an insert of a square or rectangular shape that fits into an opening of a corresponding configuration.

A distinguishing feature of certain polymer inserts of the present invention is that they can be located in a non-threaded opening or a non-threaded part of the opening. The insert of the present invention is preferably used to eliminate the wobble of the screw in the opening. Preferably the insert provides an additional means of stabilization of a screw in the opening, without interfering with the ability of the screw to insert into the opening at a range of angles.

Structures according to certain aspects of the present invention are used preferably in the treatment of bone fractures of tubular bones. In preferred embodiments, such structures can be used advantageously in the treatment of the proximal fractures, particularly humeral proximal fractures. In one embodiment, such structures are beneficial for stabilizing and healing bone tissue, where, for example, limited amount of bone tissue, or bone tissue of poor quality is present. The combination of the metal female threads and the insert acts to hold and stabilize the screw in a fixed position relative to the nail. If bone purchase is lost, the screw does not back out, and reduction of the fracture is not lost.

Structures according to various aspects of the present invention are useful for stabilization of a variety of intramedullary nail systems. Additionally, the use of the inserts according to various aspects of the current invention in various screw constructs used for attachment and stabilization of bones and soft tissues is envisioned. The constructs include but are not limited to a variety of intramedullary rods or nails, such as distal femur in retrograde femoral nails, distal humerus in retrograde humeral nails, proximal tibia in antegrade tibial nails, retrograde tibia in tibia nails.

Also within the scope of the present invention are methods of treating fractures of tubular bones using intramedullary nail systems of the present invention. Methods of the present invention comprise reaming the intramedullary canal of the tubular bone, inserting an intramedullary nail of the present invention into the tubular bone, and stabilizing the intramedullary nail in the bone by securing at least one screw in the bone with its one end and, with its second end, securing the screw in an opening of the intramedullary nail, wherein the opening contains a insert of the present invention. In accordance with such methods, the intramedullary nail systems of the present invention, in addition to an intramedullary nail and at least one screw, comprise such optional components as a tool for reaming out the intramedullary canal, tools or devices for guiding the nail through the intramedullary canal, tools or devices for securing the screws in the bone or the nail, tools for aligning or positioning components of the system with respect to the bone or each other, or any combinations or variation thereof. Any methods of attachment and stabilization of bones and soft tissues that use the inserts of the present invention are also encompassed within the scope of the present invention.

Methods of manufacturing intramedullary nails or other systems for attachment of bones and soft tissues, which comprise inserts of the present invention, are also envisioned. In a preferred embodiment, an intramedullary nail of the present invention is produced by threading the proximal holes on the lateral side of the nail and inserting the polyethylene insert into the proximal holes on the medial side of the nail. In an alternative method of manufacturing, the inserts are machined and press-fit into place or molded directly into the nail.

Additional features, objects, and advantages of the invention will become apparent from the drawings and the detailed description of the preferred embodiments.

DETAILED DESCRIPTION

Figure 1:
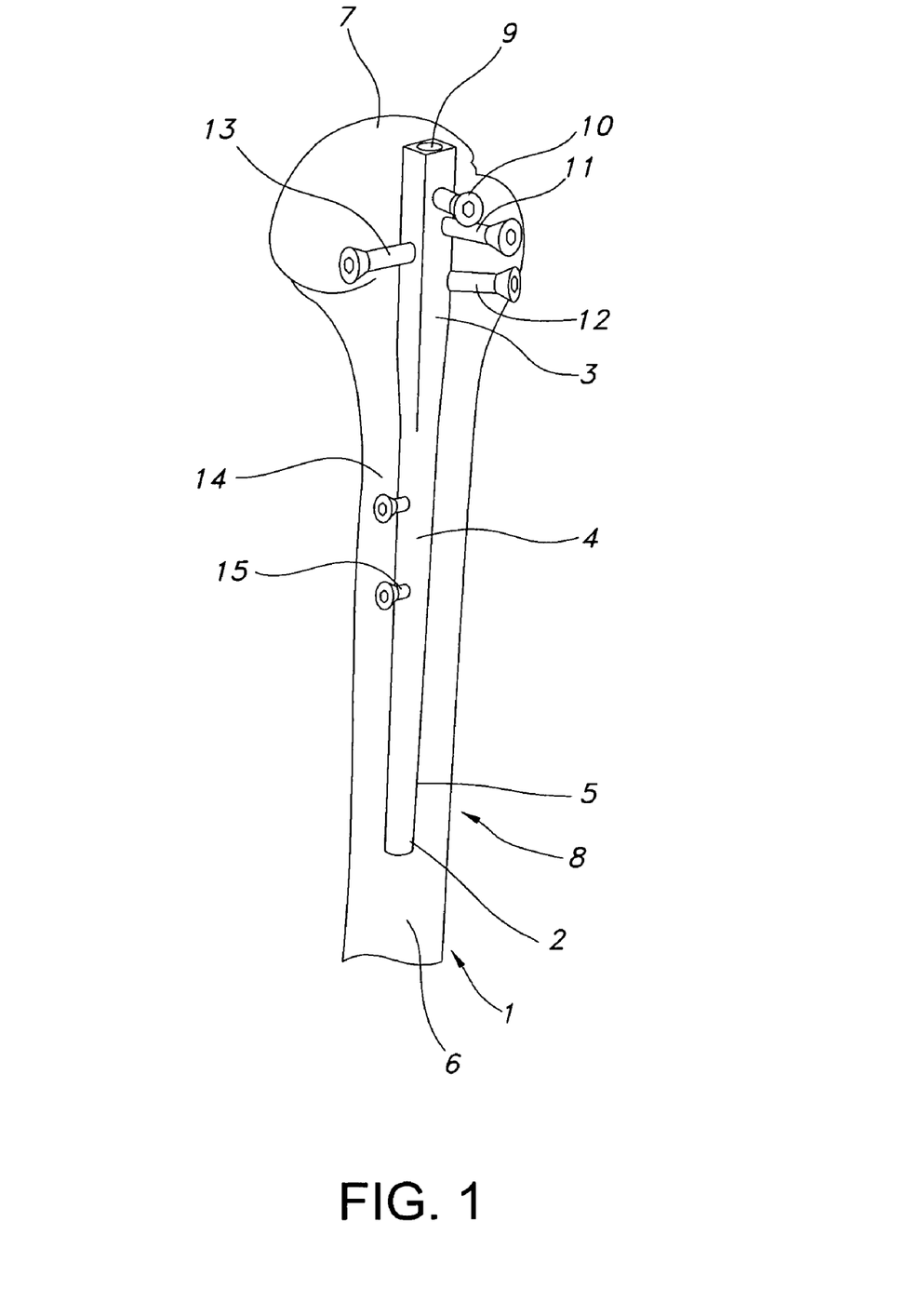
FIG. 1 is a schematic lengthwise view of the humerus, showing an intramedullary nail according to a preferred embodiment of the present invention, stabilized in the proximal section the bone with screws in multiple planes.

FIG. 1 shows humerus (1) with an intramedullary nail (2) according to a preferred embodiment of the present invention inserted. The nail takes form of an elongated unitary or integral cannulated body having a head (3), an intermediate body portion (4) and a distal tip portion (5). As shown in FIG. 1, the nail is inserted into the medullary canal of the humerus (6) to a position in which head (3) is in the proximal region (7) of the humerus, and the distal tip (5) is in the distal region (8) of the humerus. The nail (2) is cannulated or hollow along its length in order to provide an axial opening which extends the length of the nail and through the upper end of the head (3) and the lower end of the distal tip (5). The nail is a length of from approximately 160 mm to approximately 280 mm. The nail is tapered. The thickness of the walls of the nail is variable. Referring to FIG. 1, the nail (2) is inserted into the humerus to a position in which the top end of the head (3) is adjacent to or, preferably, flush with, the entry opening formed in the humeral head (3).

The head of the nail (3) has an arrangement (9) for securing the head of the nail to a device or a tool used for inserting the nail into the medullar canal. Several screw receiving openings (10-15) are located along the length of the nail. In the head of the nail (3) there is one or more screw-receiving openings, preferably in multiple planes. The opening to receive the screws proximally is threaded, with a major diameter of approximately 0.207", which is approximately 0.010" larger than a major diameter of the screw. Distally, the holes are approximately 0.147" in diameter and are adapted to receive approximately 3.5 mm screws.

For fractures of the proximal region of the humerus, the medullary canal of the humerus is reamed with an appropriate tool or device according to conventional methods and procedures. The nail is inserted into the canal using conventional methods and appropriate tools and devices, including guiding devices, such as guiding wires. Following the insertion of the nail into the medullary canal, the screws are inserted through the bone and into the openings. For fractures of proximal humerus, the screws are inserted into the proximal openings.

Figure 2:
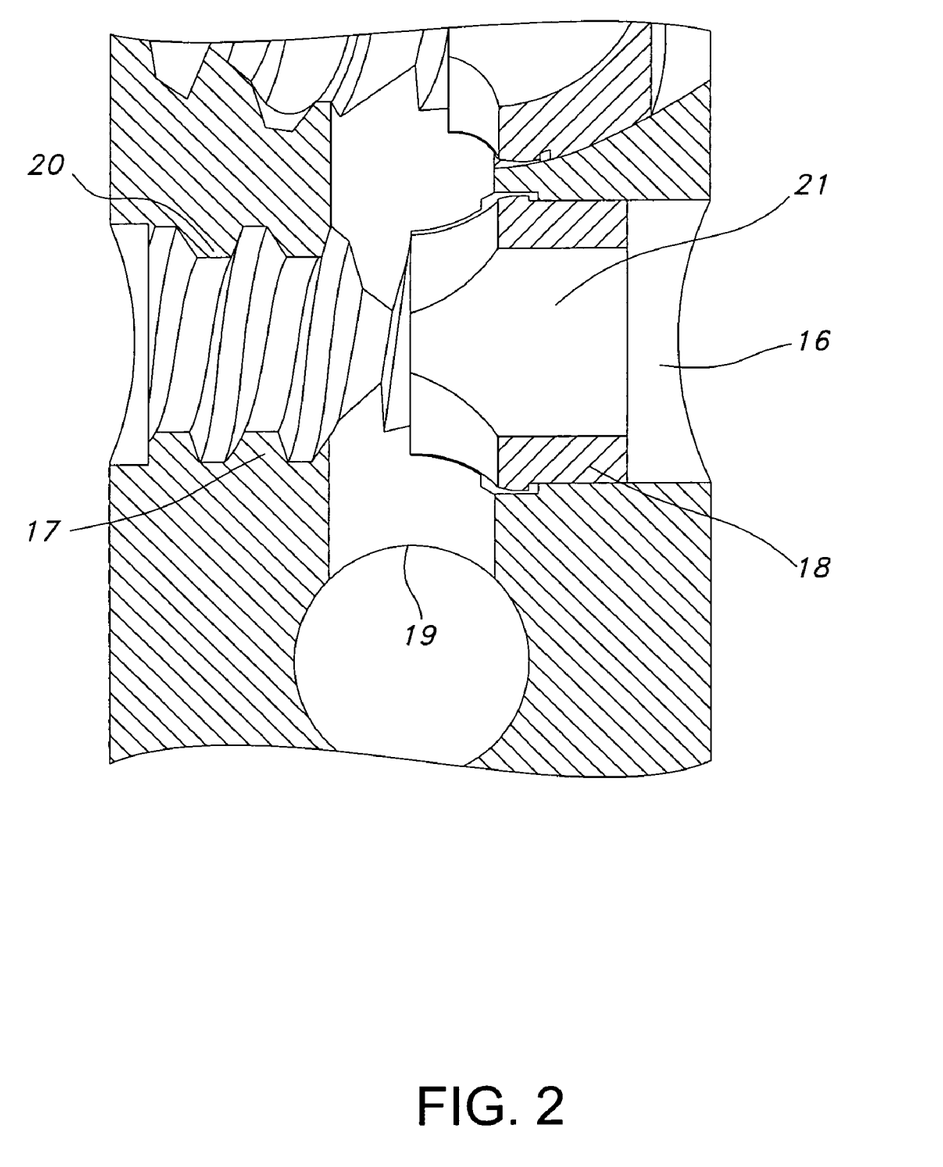
FIG. 2 is a schematic lengthwise cross-sectional view of a proximal section of an intramedullary nail, showing a transverse proximal opening in the nail with an insert stabilized with a rib.
Figure 5:
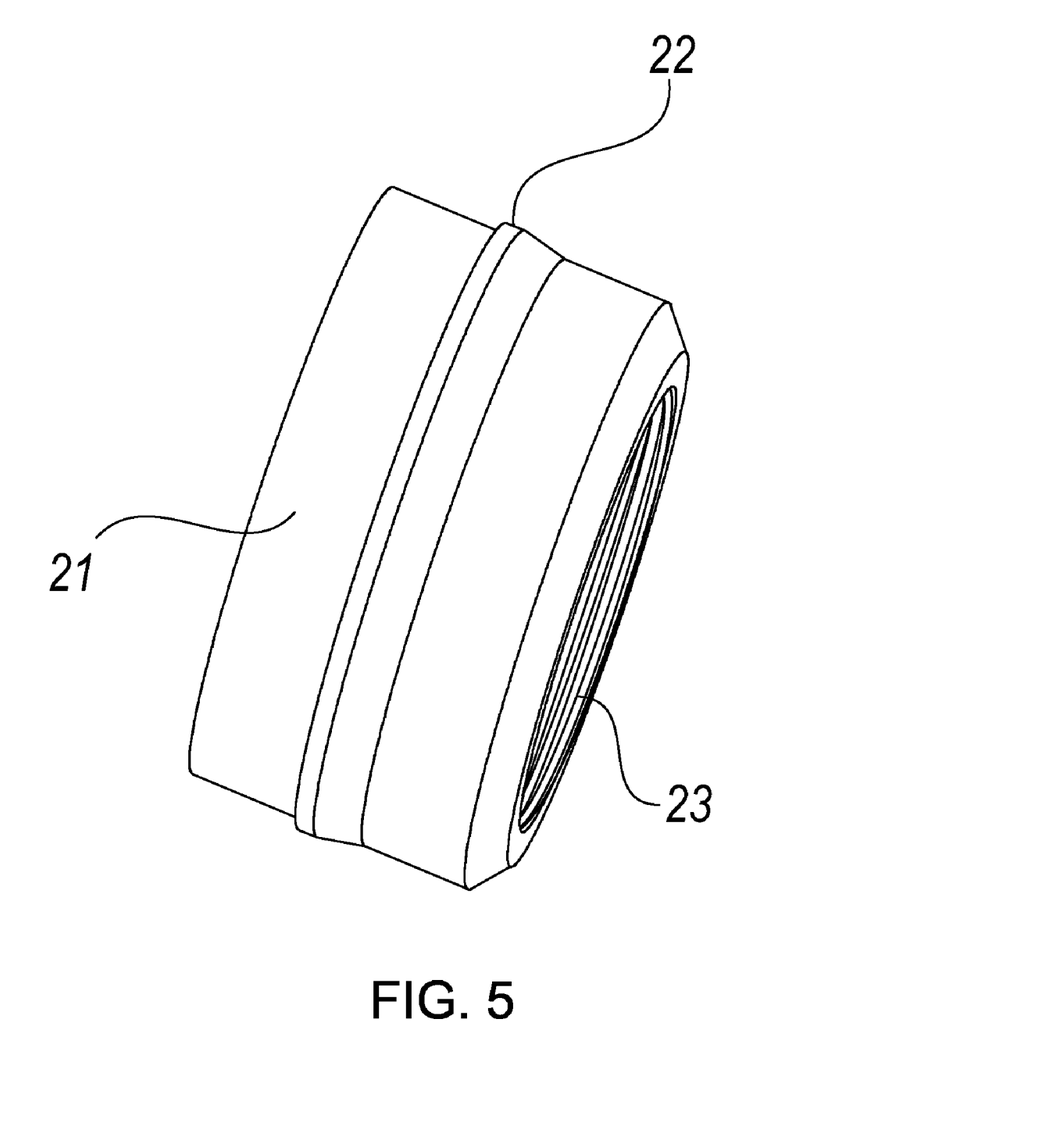
FIG. 5 is a schematic three-dimensional view of a threaded insert.

FIG. 2 shows a schematic lengthwise section of a proximal part of the humeral intramedullary nail with a transverse opening (16). The proximal part has a lateral side (17) and a medial side (18). The opening transverses both the lateral side (17), and the medial side (18), passing through the internal channel (19) of the nail. As shown in FIG. 2, the lateral side or portion of the opening has internal threads (20) for securing the screws. Female threads of the opening are of larger size than male threads of the screw, thereby allowing the screw to insert at various angles into the threaded opening. At the medial side or portion (18) of the opening, an insert (21) is placed. As shown in FIG. 5, the insert itself may be threaded (23) to match the threading on the lateral portion of the opening.

Figure 3:
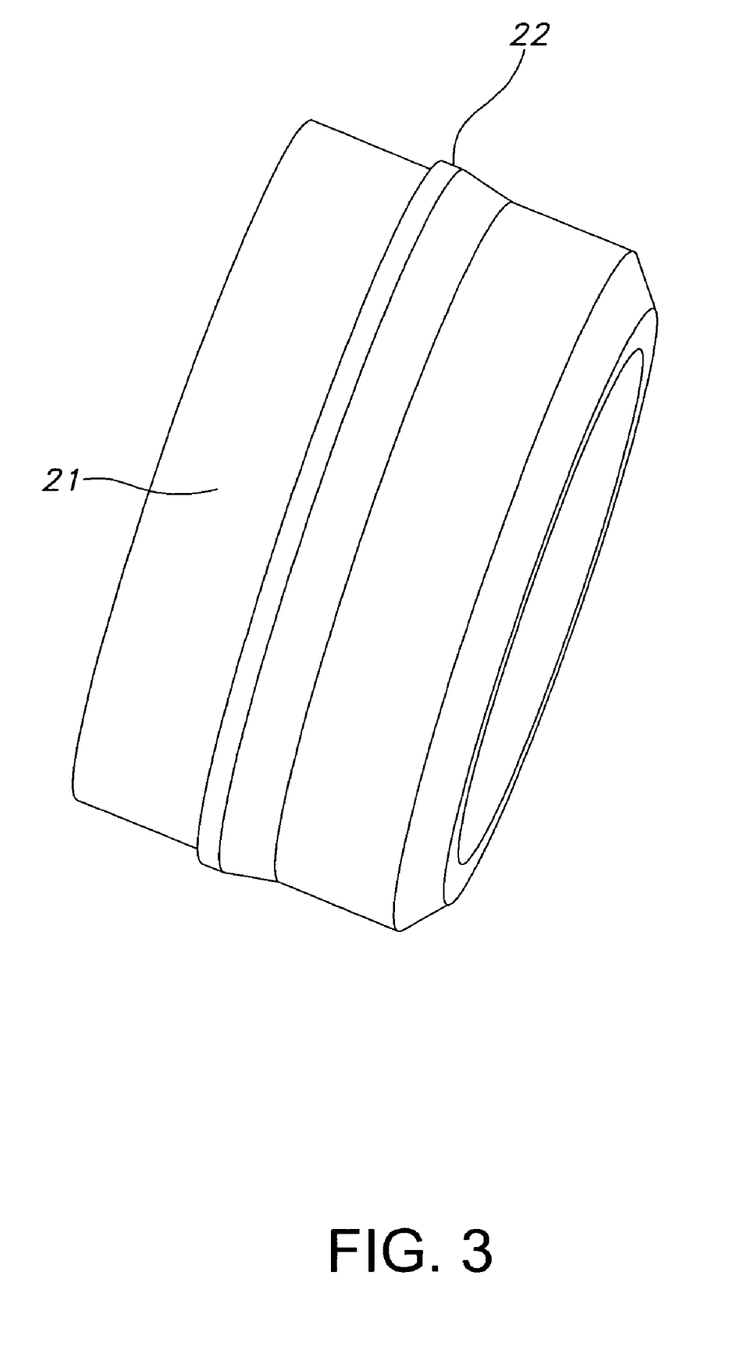
FIG. 3 is a schematic three-dimensional view of an insert.

As shown in FIGS. 2 and 3, the insert (21) is preferably of a generally cylindrical shape, with the ends preferably but not necessarily adapted to be flush with the outer surface of the nail and surface of the nail internal channel. The insert preferably features a circumferential rib (22) around its outer surface. The rib is inserted into a corresponding groove around the surface of the medial side of the opening. Alternatively, structures of various shapes and sizes may be used to secure the insert within the nail and/or prevent the insert from moving or rotating during insertion of a screw into the opening. For example, one or more longitudinal grooves or extensions could be formed on the outside of the insert to resist rotation as the screw as it is inserted through the insert. By preventing rotation, the longitudinal structures also prevent the insert from being pushed through the hole.

Figure 4:
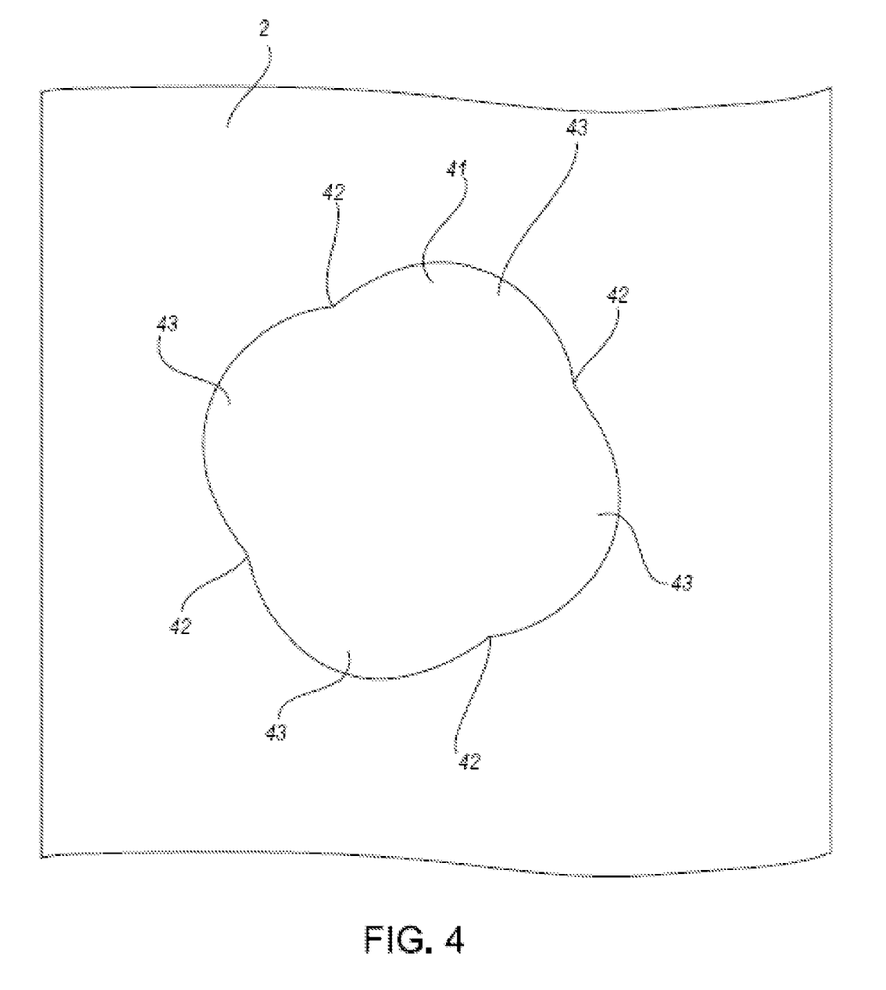
FIG. 4 is a cross sectional view of an embodiment of an intermittent groove provided in the nail of FIG. 1.

As illustrted in FIG. 3 and FIG. 4, an insert 21 of FIG. 3 may also be secured by an intermittent groove (41) around the surface of the medial side of the opening of nail (2) that may prevent the insert (21) from moving or rotating. For example, the circumferential groove as described previously would no longer be annular, but would instead start and stop leaving portions of the original surface as sharp points (42) that would engage the annular rib (22) and resist rotation. The portions (43) of the groove (41) still remaining would limit the insert (21) from being pushed out of the hole.

The screw enters the opening at the lateral side (17) of the nail, and rotates through the threaded lateral side of the opening, thus engaging the threads. After the tip of the screw passes through the threaded part of the opening, it enters the insert. As the screw continues rotating through the lateral side of the opening, the portion of the screw that exits the lateral side, proceeds to enter the insert.

The combination of the metal threads in the lateral side of the opening and the insert in the medial side of the opening holds and stabilizes the screw in a fixed position relative to the nail. The threads in the opening of the nail are, in certain embodiments, not sufficient to stabilize the nail as they are designed to allow insertion the screw into the opening at a range of angles. However, the insert receives and stabilizes the screw, in combination with the threads in the opening at whatever angle the screw is inserted into the opening. The insert eliminates the need to rely on the purchase of the screw to the bone for stabilization. Thus, nails according to preferred embodiments of the invention are distinguishable from conventional nails, where the screw relies on the purchase of its part outside of the nail to the bone, thus suffering from the problem that the stabilization decreases with the decrease of the purchase to the bone.

The use of nails according to certain aspects of the invention in either the right or the left humerus is permitted because such nails are symmetrical about a vertical plane perpendicular to the axis of the humeral neck. To facilitate the insertion of the screws into the nail, the openings for the screws can be made, reamed, bored or otherwise produced in the bone or its fragments. Screws used in the intramedullary nail system according to preferred embodiment of the invention are preferably self-threading screws, although the openings in the bone or its fragments can be partially pre-threaded. Preferred but not limiting materials for the nail are stainless steel or titanium, PEEK with carbon fiber, or nitinol.

The foregoing discloses preferred embodiments of the present invention, and numerous modifications or alterations may be made without departing from the spirit and the scope of the invention.

What is claimed is:

1. An intramedullary fixation device comprising:
   an intramedullary nail having an opening for receiving a screw, the opening comprising a first portion on a first side of a cannulation through the intramedullary nail and a second portion on an opposing side of the cannulation, the first portion of the opening comprising an intermittent groove; and
   an insert incorporated into the first portion of the opening, the insert comprising a hollow portion and a circumferential rib around an outer surface of the insert, the circumferential rib interacting with the intermittent groove of the first portion of the opening to secure the insert within the opening of the intramedullary nail and prevent the insert from moving and rotating during insertion of the screw into the opening.

2. The intramedullary fixation device of claim 1 wherein the second portion of the opening of the nail is not covered by the insert.

3. The intramedullary fixation device of claim 2 wherein the second portion of the opening is threaded.

4. The intramedullary fixation device of claim 2, wherein the screw comprises threads and the second portion of the opening comprises threads, wherein the relative sizes of the threads of the second portion of the opening and the threads of the screw are adapted to allow insertion of the screw within the opening at a range of angles.

5. The intramedullary fixation device of claim 4, wherein the intramedullary nail and the threads of the second portion of the opening comprise stainless steel, titanium, PEEK with carbon fiber, or nitinol.

6. The intramedullary fixation device of claim 1, wherein the insert is made of a polymer material.

7. The intramedullary fixation device of claim 1, wherein the hollow portion of the insert is threaded.

8. The intramedullary fixation device of claim 1, wherein the first portion of the opening is non-threaded.

9. The intramedullary fixation device of claim 1 wherein the screw comprises threads and the second portion of the opening comprises threads, wherein the relative sizes of the threads of the second portion of the opening and the threads of the screw are adapted to allow insertion of the screw within the opening at a range of angles.

10. The intramedullary fixation device of claim 9, wherein the intramedullary nail and the threads of the second portion of the opening comprise stainless steel, titanium, PEEK with carbon fiber, or nitinol.

11. The intramedullary fixation device of claim 1 wherein:
the first side is on a medial side of the intramedullary nail; and
the second side is on a lateral side of the intramedullary nail.

12. An intramedullary fixation device comprising:
an intramedullary nail having an opening for receiving a screw, the opening comprising a first portion on a medial side of the intramedullary nail and a second portion on a lateral side of the intramedullary nail, the first portion of the opening comprising an intermittent groove defining a plurality of substantially sharp points separated by insert retaining portions; and
an insert that engages the intermittent groove, the insert comprising a hollow portion and a circumferential rib encircling an outer surface of the insert, wherein the substantially sharp points of the intermittent groove engage the circumferential rib to rotationally stabilize the insert relative to the opening and wherein the insert retaining portions receive portions of the circumferential rib to retain the insert within the opening;
wherein, when the screw is inserted into the opening, the insert helps stabilize the screw in a fixed position relative to the intramedullary nail.

13. An intramedullary fixation device comprising:
an intramedullary nail having an opening for receiving a fastener, the opening comprising a first portion on a medial side of the intramedullary nail and a second portion on a lateral side of the intramedullary nail, the first portion of the opening comprising an intermittent groove; and
an insert that engages the intermittent groove, the insert comprising a hollow portion and a circumferential rib encircling an outer surface of the insert, wherein the intermittent groove engages the circumferential rib to rotationally stabilize the insert relative to the opening and receives portions of the circumferential rib to retain the insert within the opening.

14. The intramedullary fixation device of claim 13, wherein the intramedullary groove defines a plurality of substantially sharp points separated by insert retaining portions.

15. The intramedullary fixation device of claim 14, wherein the substantially sharp points of the intermittent groove engage the circumferential rib to rotationally stabilize the insert relative to the opening.

16. The intramedullary fixation device of claim 14, wherein the insert retaining portions receive portions of the circumferential rib to retain the insert within the opening.

* * * * *

UNITED STATES PATENT AND TRADEMARK OFFICE
CERTIFICATE OF CORRECTION

PATENT NO.       : 7,655,009 B2                                    Page 1 of 1
APPLICATION NO. : 10/999572
DATED            : February 2, 2010
INVENTOR(S)      : N. Kelley Grusin It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1222 days.

Signed and Sealed this

Twenty-third Day of November, 2010

David J. Kappos
*Director of the United States Patent and Trademark Office*